United States Patent [19]

Kellogg et al.

[11] 4,251,779
[45] Feb. 17, 1981

[54] FREQUENCY SYNTHESIZER APPARATUS AND METHOD IN ULTRASONIC IMAGING

[75] Inventors: Seeley C. Kellogg, Durham; Philip J. Peluso; Richard B. Bernardi, both of Cheshire, all of Conn.

[73] Assignee: Picker Corporation, Cleveland, Ohio

[21] Appl. No.: 970,662

[22] Filed: Dec. 18, 1978

Related U.S. Application Data

[62] Division of Ser. No. 879,236, Feb. 21, 1978, Pat. No. 4,169,385.

[51] Int. Cl.³ .............................................. H03L 7/08
[52] U.S. Cl. ..................................... 331/1 A; 331/14; 328/14
[58] Field of Search ................... 331/1 A, 14, 18, 25; 328/14; 307/271

[56] References Cited

U.S. PATENT DOCUMENTS

| 3,806,826 | 3/1974 | Schlosser | 331/1 A |
| 3,825,855 | 7/1974 | Bassett et al. | 331/14 X |
| 3,890,871 | 6/1975 | Oberheim | |
| 4,123,724 | 10/1978 | Das et al. | 331/1 A |

FOREIGN PATENT DOCUMENTS

| 1376286 | 12/1974 | United Kingdom . |
| 1386935 | 3/1975 | United Kingdom . |
| 1410363 | 10/1975 | United Kingdom . |
| 1423421 | 2/1976 | United Kingdom . |
| 1509530 | 5/1978 | United Kingdom . |

Primary Examiner—Siegfried H. Grimm
Assistant Examiner—Edward P. Westin
Attorney, Agent, or Firm—Watts, Hoffmann, Fisher & Heinke Co.

[57] ABSTRACT

A frequency program synthesizing apparatus and method is disclosed for controlling delay circuitry in ultrasonic imaging systems. Each frequency program synthesizer includes an adjustable frequency source for producing the clocking signals and a multichannel memory having a plurality of address channels each allocated for digitally storing a signal representing the frequency corresponding to one of said frequency program steps and circuitry for applying the stored signals in a sequence to cause the adjustable frequency generator to produce the frequency program. Each program synthesizer also includes updating circuitry for adjusting the values of the stored digital frequency representations to compensate for undesirable differences between the frequency of the generated program and a set of predetermined program frequency steps.

10 Claims, 11 Drawing Figures

FREQUENCY SYNTHESIZER APPARATUS AND METHOD IN ULTRASONIC IMAGING

This is a division of application Ser. No. 879,236 filed Feb. 21, 1978 now U.S. Pat. No. 4,169,385.

BACKGROUND OF THE INVENTION

Field of the Invention

This invention relates generally to the field of ultrasonic imaging techniques in which ultrasonic energy is utilized to produce a visual image of internal structure of a subject. More particularly, the invention relates to improved apparatus and method for synthesizing precisely controlled programs of clock signal frequencies used to operate certain delay circuitry in imaging electrical circuitry of such ultrasonic imaging systems.

Typically, such ultrasonic systems include a multielement transducer, a display, and intervening imaging electronic circuitry. The transducer produced ultrasonic energy which is directed into the subject, and produces electrical signals representing characteristics of ultrasonic echoes produced by the incident energy at interfaces between tissues of differing nature within the subject. The imaging electronics processed the electrical echo-representing signals from the transducer so that they can be employed to actuate the display (such as a cathode ray oscilloscope) to produce a visual representation of structure within the subject.

A known mode of operation of a system such as the one described above is called "B scanning". In B scanning, the transducer is actuated by the imaging electronics to direct pulses of ultrasonic energy into the subject along a beam path. Synchronously with the production of each pulse, the imaging electronics causes the display oscilloscope to initiate a trace in the form of an electron beam and to move the electron beam in a trace across the oscilloscope screen in a direction which is a function of the direction of the ultrasonic beam path.

When an ultrasonic pulse of energy traverses an interface within the subject between tissues of differing acoustical characteristics, an ultrasonic echo is produced, which is utilized to modulate the intensity of the electron beam trace to derive a visual indication on the display or beam trace to derive a visual indication on the display of the location and characteristic of the interface within the subject as expressed by the echo intensity.

This occurs by virtue of the fact that some of the energy from the ultrasonic echoes is directed back toward, and is received by, the transducer. In response to the receipt of the ultrasonic echos, the transducer produces electrical signals which are processed by the imaging electronics and thereby employed to modulate the intensity of the electron beam trace of the display to produce the indication of the location and characteristic of the interface.

An operator using a B scanning apparatus, by moving the transducer about the periphery of a subject in a common place through the subject, can "paint" an image on the oscilloscope of internal subject structure in the plane.

It is known to employ the multiple elements of the transducer to the receipt of ultrasonic echoes in a particular region. A proposal for doing this involves the use of a transducer having several concentric annular transducer elements. The transducer elements are separately connected to the imaging electronics so that they can be independently actuated to produce the incident ultrasonic beam. Similarly, the individual transducer elements are electrically segregated so that electrical signals they produce from the ultrasonic echoes can be separately processed.

The focusing of the transducer sensitivity in a predetermined region is accomplished by appropriately delaying the signals from the various transducer elements relative to one another. This delay is accomplished by the use of separate delay circuit elements interposed in each of the various individual electrical circuit connected respectively to each of the transducer elements.

In order to focus the sensitivity of the transducer at a particular distance from the transducer, the delay circuits connected to the respective transducer elements are operated to establish a predetermined pattern of delay among the circuits. This delay pattern is selected such that the electrical signals produced by each transducer element in response to echoes emanating from within the predetermined region are placed in phase with one another. This co-phasing of the electrical signals produced by the transducer enables these signals to reinforce one another, rather than to interfere with one another as would be the case if the signals were not appropriately phase delayed. This reinforcement of the various electrical signals tends to intensify their combined amplitude, and renders the ultrasonic system generally more sensitive to ultrasonic echoes emanating from within the predetermined region than would be the case without the appropriate delay pattern.

It is also known to provide means for time varying the distance from the transducer of the predetermined region of heightened sensitivity. If the predetermined region of optimum sensitivity is caused to recede outwardly from the transducer, beginning with the initiation of a particular ultrasonic energy pulse, and the speed of movement of the region equals the acoustic velocity in the subject, reception of the echoes is enhanced. The enhancement of reception occurs because the predetermined region of optimum sensitivity is caused to coincidentally recede into the subject with the incident wavefront in response to which ultrasonic echoes are created.

Specific techniques for deriving concrete delay patterns such as described above are explained by Walker, J. T. et al in "Digitally Controlled CCD Dynamically Focused Phased Array" 1975 Ultrasonics Symposium Proceedings, I.E.E.E. Cat. #75 CHO 994-45U, expressly incorporated here by reference.

For the previously described "fixed focus" system, where the region of enhanced sensitivity is located in one particular place, fixed delay lines are used. These fixed delay lines are hard wired circuitry including series connected branches having capacitive and resistive circuit elements. In such delay lines, an electrical pulse appearing at one end of the series of delay line branches requires a predetermined time to pass to an output connected to the last of the series connected elements. An advantage of these fixed delay lines is their relative economy and simplicity. In fixed focus systems, where the delay in the transmission of electrical signals from each of the transducer elements can be constant, and the delay need not vary, these fixed delay lines are acceptable means for accomplishing the delay.

Where, however, it is desired to time vary the focal distance of the transducer's region of sensitivity, and time variable delays must be applied to the various electrical signals emanating from the respective transducers, other means must be used to effect these delays.

It is known to use delay circuitry in such instances in which input pulses pass through the delay circuitry element in a time which is a function of the frequency of a clocking signal which is applied to that delay circuitry. Accordingly, in order to vary the delay time of a particular delay element, it must be possible to alter the frequency of the clocking signal applied to that element.

It is obvious that in an application such as the ultrasonic system described herein, the delay times of the various delay lines employed must be made to vary with extreme rapidity in order to adjust the delay rapidly enough to accomplish the desired change of the focal distance. In practice, it has been determined that it is often necessary to employ use times for the various clocking frequencies applied to the delay elements of as little as 100 microseconds or less.

Existing technology has not yielded apparatus which can accomplish the very rapid frequency changes in the clocking signals with the precision required.

One proposal for controlling these frequencies has been to employ circuitry known as a phase locked loop. Such circuitry typically employs a constant frequency source along with a voltage controlled oscillator. A voltage controlled oscillator is a device which produces an alternating output signal whose frequency is a function of an analog voltage level input to the voltage controlled oscillator. A phase locked loop also employs a phase detector which produces an analog output whose magnitude is a function of the difference in phase between two input signals. The output of the phase detector is connected to the input of the voltage controlled oscillator and its inputs are the output from the constant frequency source and the output from a variable divider circuit. The variable divider circuit produces an alternating signal having a frequency which is a submultiple of the frequency of the output which is applied to the divider. In a phase locked loop, the input to the variable divider is derived from the output of the voltage controlled oscillator and the output of the variable divided is directed as one input to the phase detector.

A phase locked loop such as described here can be used to generate an output signal having a frequency extending between a range of F1 to F2 in N discrete steps separated by a frequency difference D. When so employed, the constant frequency source is selected to produce a signal having a frequency D. The variable divider circuit is adjustable in steps to produce a signal having a frequency of F down to F/N where the variable divider is set to dive by integers from 1 to N.

It has been determined, however, that a phase locked loop is generally not useful for controlling frequencies in the environment of an ultrasonic system such as described here. This is because the phase locked loop lacks the required circuit stability to accomplish precise frequency control of its output with the rapidity dictated by the very short use times appropriate in employment in these ultrasonic systems. In present technology, the time for a phase locked loop to lock onto and stabilize at a particular frequency output exceeds considerably the stringent requirement of use times of 100 microseconds or less. It is simply not possible to synthesize a series of programmed frequencies with use times as short as those desired in this application by the use of a phase locked loop. In fact, it is not known that any type of previously existing circuitry could synthesize such frequencies precisely with the required brevity of use time.

SUMMARY OF THE INVENTION

The invention here described and claimed includes a circuitry designed for accurately synthesizing a program of frequencies which can be very rapidly changed from one selected frequency to another, and with no appreciable settling or stabilization time following the frequency changes.

More specifically, the invention of this application includes method and apparatus for producing a precisely controlled program of frequencies of electrical clocking signals. The apparatus includes a variable frequency generator for producing a succession of the alternating electrical signals to be frequency controlled, and a multichannel memory for storing digital representations of each desired frequency of the program. The apparatus further comprises circuitry for applying the digital representations to operate the variable frequency generator to produce the program.

A more specific aspect includes update circuitry for adjusting the values of the digitally stored representations to compensate for undesirable changes in the program frequencies generated from predetermined program frequencies.

The update circuitry includes a fixed frequency source and a clock for defining a predetermined time period which is a function of the frequency of the adjustable generator at a predetermined program frequency step. The circuit also includes means for counting the number of fixed frequency cycles produced during the predetermined period, and means for indicating the number of such cycles (a reference number) which would be ideally produced in the predetermined period at the particular program step. Also included is a comparator for adjusting the value of the associated digitally stored signal in response to sensed difference between the counted and the ideal number of reference signals.

According to another aspect, the apparatus includes means for producing a succession of the alternating electrical signals to be frequency controlled, and means for sampling the signals during a brief time increment. The apparatus further comprises circuitry for comparing the sampled signal frequency with a reference representing a preferred reference frequency.

The circuitry of this invention enables sampling and comparison of the frequency of a synthesized signal within a time interval substantially within the desired use time of the individual steps of the program of frequencies. The error signals produced each represent a very small increment in frequency for use in subsequent correction. Therefore the device corrects the frequency by only a very small increment at a time. These minute corrections can be accomplished very rapidly with a minimum of settling or stabilization time required, because of their small magnitudes, and the fact that the corrections take place during system "dead time", between the ultrasonic pulses produced by the system.

According to a more specific aspect of the invention, the sampling step is accomplished in substantially less than 10 microseconds.

In accordance with another more specific aspect, the comparison and storage operations are executed digitally, rather than in analog form, such as in a phase locked loop. The digital nature of these operations is less susceptible to the need for settling time than are similar analog operations.

According to another specific aspect, the program of synthesized signals is a periodic stair-step time function having discrete frequency levels and a uniform use time for each frequency level. In this aspect, the sampling operation is performed entirely within one of the use times, or step widths, while the correction step in response to an error signal generated during the sampling step is executed, not instantaneously, but rather in the corresponding dead time.

With respect to another specific aspect of the invention, the adjustable frequency generator is controlled by a digital-to-analog converter, and the error signal, in response to which the correction occurs, is limited to only one least significant bit of the digital-to-analog converter. This feature assures the precision of the frequency selection process to within that one least significant bit.

Moreover, the short term stability of the adjustable frequency generator is such that the frequency generator does not require any substantial settling or stabilization time when corrected by an amount represented by a change of one least significant bit. "Short term" is determined to be the time duration of a use time, i.e., a step width.

In accordance with another specific feature the apparatus of this invention operates by adjusting the frequency produced by the adjustable frequency generator in discrete amounts, each of which is much less than one-half of the signal frequency. This feature is related to the more general features wherein the correction of frequency is made in steps so small that substantial transients or upset of the frequency synthesizing circuitry is avoided.

Another feature of the invention includes repetitively sampling the output of the adjustable frequency generator and producing error signals each indicating a minute frequency change, and updating a memory used to produce the desired frequency of each frequency level of the program by a running accumulation of the error signals. In this way, the correction of the frequency output of each frequency level can be maintained by adjusting the frequency in only very small increments, enhancing the resistance of the system to the generation of transients as described above.

This invention will be understood in more detail by referring to the following detailed description and claims, and to the drawings, in which:

DESCRIPTION OF THE PREFERRED EMBODIMENT

Figure 1:
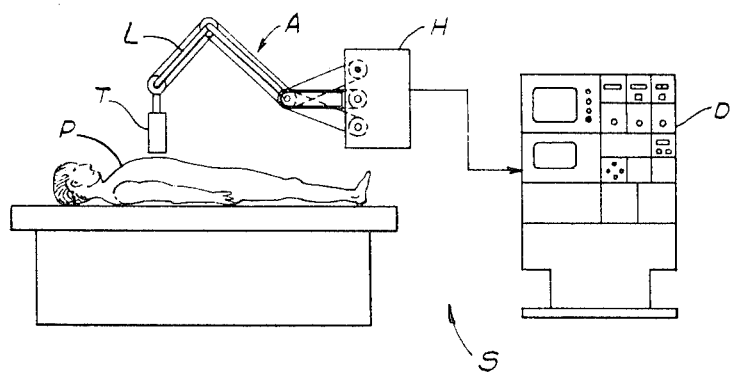
FIG. 1 is a simplified drawing of an ultrasonic imaging system incorporating the present invention.

FIG. 1 shows an ultrasonic imaging system S in which the present invention is applicable. The system S includes an ultrasonic transducer T supported by movable arm structure A and connected by electrical leads L to a support housing H. The system S also includes a display unit D, containing imaging electronics connected to the transducer leads L.

The system S directs bursts of ultrasonic energy into a subject, such s a patent P, and derives visual images representing internal structure of the body of the patent P which are produced on a screen of the display unit D. The ultrasonically derived images are produced from ultrasonic echoes occurring in response to the bursts of ultrasonic energy directed into the body of the patient P by way of transducer T. The transducer T receives some of the energy from these ultrasonic echoes, and produces electrical signals representing the echoes which are transmitted over the leads L to the imaging electronics located within the unit D. The imaging electronics processes the electrical signals and employs them to actuate the display D to produce the ultrasonically derived image of internal subject structure.

Figure 2:
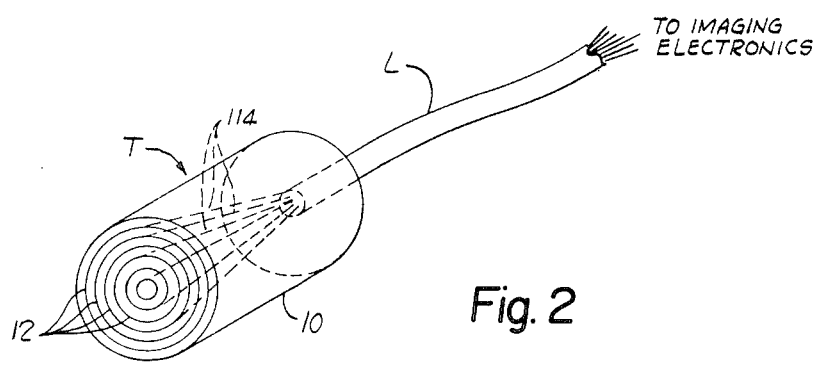
FIGS. 2 and 3 are graphical illustrations showing a portion of the system illustrated in FIG. 1.
Figure 3:
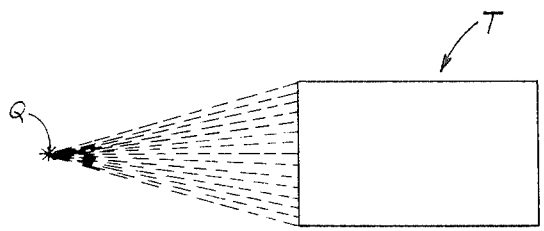

The transducer T is illustrated in more detail in FIGS. 2 and 3. FIG. 2 illustrates the transducer T as including a generally cylindrical housing 10 in one end of which are located a plurality of concentric annular transducer elements 12. Each of the transducer elements such as 12 is made of a particular type of piezoelectric material and each is electrically isolated from the others. Each of the transducer elements 12 is individually connected to the imaging electronics within the unit D by way of one of the several electrical leads 14 which together make up a transmission cable comprising the leads L.

When a rapidly alternating electrical potential is applied to one of the transducer elements through its associated electrical lead 14, the transducer element converts the electrical energy to mechanical oscillations, and produces ultrasonic energy which is directed outwardly therefrom. Conversely, when ultrasonic energy, such as generated from ultrasonic echoes within the patient's body, P are transmitted back to the transducer element 12, the transducer element converts the mechanical energy back to electrical energy which is transmitted as an electrical signal (representing a characteristic of the ultrasonic echo received) along the associated one of the electrical leads 14. In this way, the imaging electronics located within the unit D actuates the tranducer to produce ultrasonic energy and receives the electrical signals from the transducer elements which represent characteristics of the sensed ultrasonic echoes produced in response to the incident ultrasonic energy.

The imaging electronics also includes means for programmably delaying the electrical signals separately transmitted from the transducer over each of the electrical leads 14. The purpose of this programmed delay is to enable the co-phasing of the electrical signals produced along the leads 14 in response to an ultrasonic echo energy burst received at the transducer elements 12. The co-phasing takes place with respect to ultrasonic echoes originating from a region in the neighborhood of a point, such as Q illustrated in FIG. 3. FIGS. 2 and 3 illustrate the transducer as having seven transducer elements concentrically aligned. The central transducer element is circular in configuration while the outer size are annular, one outside the next.

In order to co-phase the electrical signals produced in response to an ultrasonic echo emanating from a neighborhood around a point Q axially aligned with the transducer T, delay elements, explained in more detail below, are used. One delay element is positioned in series with each of the electrical leads 14 to operate upon electrical signals coming from an individual transducer element.

In order to co-phase the electrical signals from the transducer elements 12, the electrical signals produced by the more centrally located of the elements must be delayed to a greater extent relative to the delay of the signals from the more outwardly located transducer elements. If one envisions ultrasonic energy propagating in phase from the neighborhood of a point Q, as illustrated in FIG. 3, it will be seen that the distance traveled by ultrasonic energy from the point Q to an outwardly located transducer element is greater than the distance required to propagate to a centrally located element. This means that the ultrasonic energy directed to the central area of the transducer elements 12 is incident upon those transducer elements before the corresponding portion of the ultrasonic wavefront reaches the more outwardly located elements. Hence, in order to co-phase the electrical signals produced by the transducer elements from the echoes originating at Q, the electrical signals produced by the central elements must be delayed in order that the electrical signals produced over the cable leads L be mutually in phase.

Figure 4:
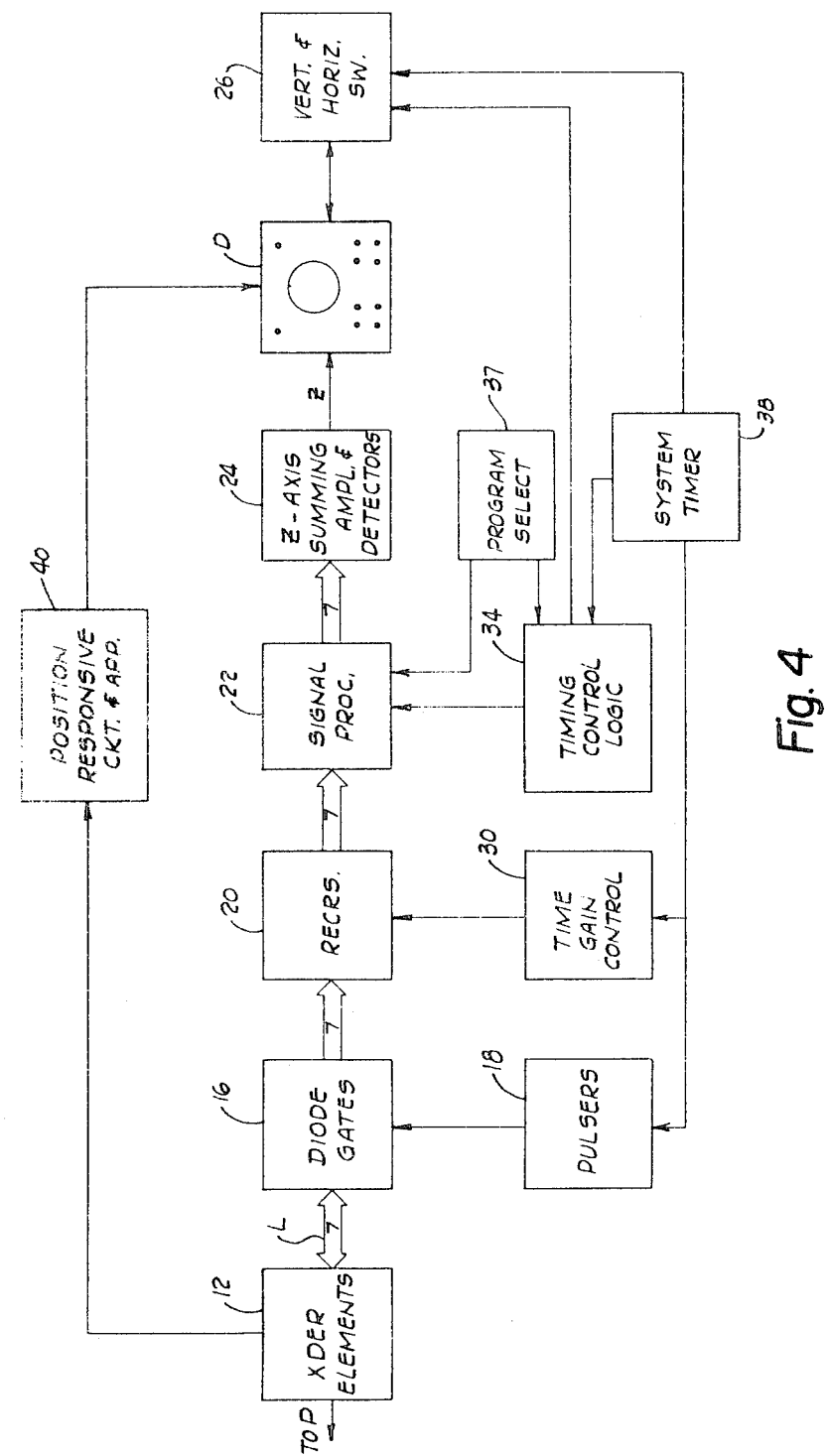
FIG. 4 is a block diagram illustrating the system shown in FIG. 1.

FIG. 4 is a more detailed block diagram illustrating the components of the system S in greater detail. In FIG. 4, the transducer elements 12 are illustrated as connected by the cable L to a set of diode gates 16. A set of pulsers 18 produces bursts of electrical energy which are directed by the diode gates through the cable L to actuate the transducer elements 12 to produce bursts of ultrasonic energy incident into the patent P.

The pulsers 18 operate at a low duty cycle. They are programmed to produce intermittent bursts of energy and to remain quiescent during the intervals between the pulse production. The purpose of this is to allow time for the ultrasonic echoes induced by the incident ultrasonic energy to return to the transducer elements to be converted to electrical signals and be processed by the remainder of the system S.

During actuation of the pulsers 18, the diode gates direct the electrical energy only toward the transducer elements 12.

Electrical signals derived from ultrasonic echoes by the transducer elements 12 are transmitted through the diode gates to a set of receivers 20. The diode gates are responsive to actuation of the pulsers to transmit the electrical energy from the pulsers only toward the transducer elements 12 during pulsing, and to block the incident pulsed electrical energy from proceeding toward the receivers 20. When the pulsers are not producing electrical energy, and the system in waiting to receive and to process electrical signals from the transducer elements, the diode gates permit the electrical signals from the elements 12 to proceed to the receivers 20.

The receivers 20 each include one adjustable amplifier to receive electrical signals from each respective transducer element.

The electrical signals amplified by the receivers 20 are passed in parallel to a signal processing unit 22, which will be described in detail below. The processing circuitry 22 includes the delay elements for co-phasing in additive phase the parallel electrical signals transmitted from the receivers 20.

The electrical signals processed by the circuitry 22, and collectively representing an amplitude of a particular ultrasonic echo phenomenon, are further transmitted to summing circuitry 24. The summing circuitry 24 includes a summing amplifier for producing a single output which is a function of the sum of the amplitudes of the incoming parallel processed electrical signals. The summing circuitry 24 also includes detection circuitry connected to the output of the summing amplifier to produce a Z axis signal to the screen of the display D. The Z axis signal indicates in analog form to the display D the amplitude of the particular echo represented by the aggregate of the electrical signals at the summing amplifier.

Vertical and horizontal switching circuitry 26 is also connected to the display D to actuate the oscilloscope to produce a raster which is modulated with the Z signal from the summing circuitry 24 to produce, with motion of the transducer T, a B-scan image describing internal subject structure.

Time gain control circuitry 30 is additionally provided and coupled to the receiver circuitry 20 to enhance the uniformity of the image produced on the oscilloscope D. The time gain control circuitry increases the gain of the amplifiers included in the receivers 20 as a function of time after the pulsers 18 initiate an incident ultrasonic burst. This increase in amplification assists in causing the amplitude of the signals from the receivers 20 to consistently represent the amplitude of the ultrasonic echoes in response to which the electrical signals are generated without regard for the distance from the transducer at which the ultrasonic echoes emanate. Thus, the time gain control circuitry 30 compensates for attenuation of ultrasonic echoes due to varying distances of the echo sources from the transducer. If it were not for the compensation of the time gain control circuitry, echoes emanating from a longer distance from the transducer would appear weaker than equally strong echoes emanating from a shorter distance from the transducer.

The system S also includes timing control logic 34 operating in conjunction with the signal processing circuitry 22 and a program select circuit in a manner to be described more fully below. A system timer 38 is coupled to the control logic 34, the time gain control circuitry 30 and the vertical and horizontal switches 26 to properly time the operation of these components in their actuation of various parts of the system S described above.

The system S also includes position responsive circuitry 40 connected between the transducer and the display D. The position responsive apparatus and circuitry 40 responds to the positions of the respective elements of the arm structure A mechanically connecting the transducer to the housing H for actuating the display D for locating a tracer spot on an oscilloscope CRT (the brightness of which is modulated with the Z axis signal) at a position which corresponds to the position of the transducer T, as the transducer T is moved in a plane about the surface of the subject patient P.

In this way, an operator of the system S can, by moving the transducer about the surface of the patient P, "paint" an ultrasonically derived picture of internal structure of the subject appearing on the oscilloscope screen. Structure embodying this aspect of the system S is described and claimed in U.S. Pat. No. 4,014,207, to Meyer, et al, issued on Mar. 29, 1977 and assigned to Picker Electronics, Inc., a subsidiary of the assignee of this application, which patent is expressly incorporated here by reference. Apparatus embodying the subject matter of U.S. Pat. No. 4,014,207 exists in an ultrasonic imaging system manufactured by Picker Corporation, Northford, Connecticut, U.S.A., and designated as Model 80L.

Figure 5:
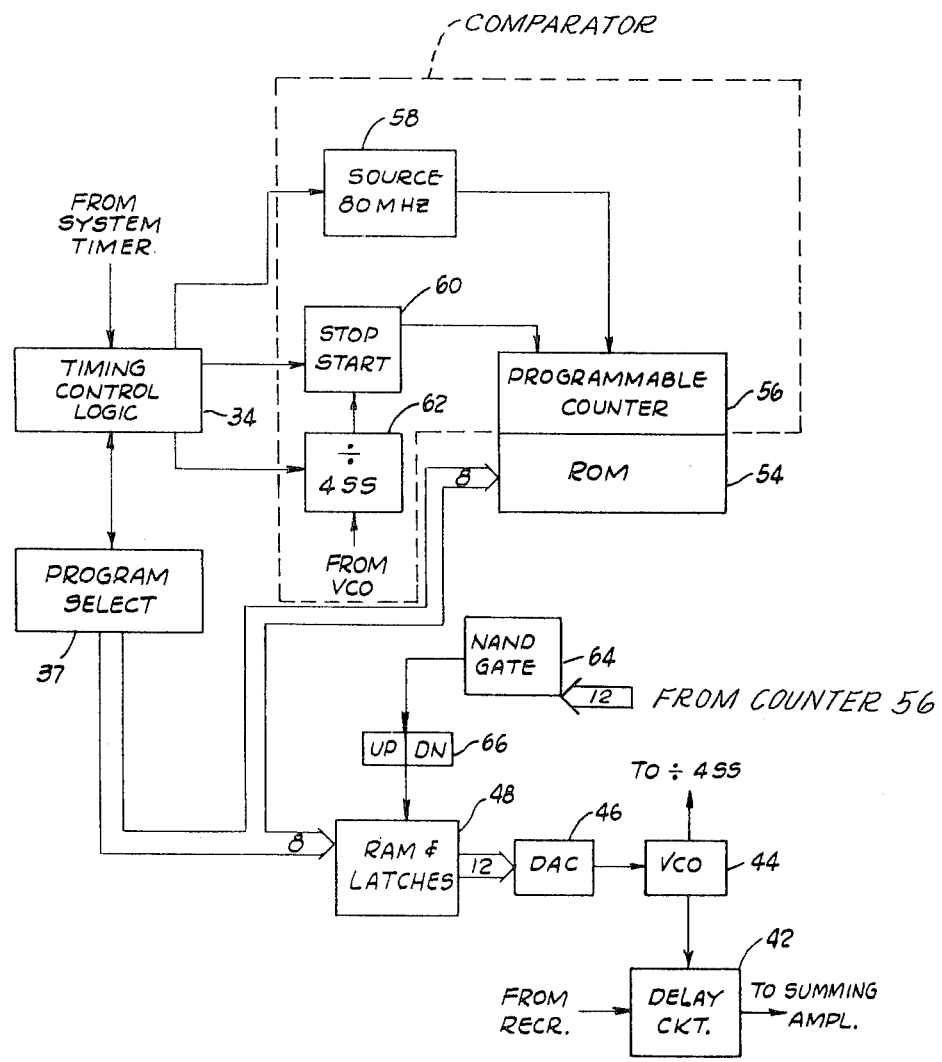
FIG. 5 is a detailed block diagram illustrating a portion of the system illustrated in the block diagram of FIG. 4.

FIG. 5 is a detailed block diagram illustrating the timing control logic 34, program select circuitry 37 and the signal processing circuitry 22 illustrated in FIG. 4, and the manner of connection of this circuitry to the remainder of the system S.

The signal processing circuitry 22 incorporates a total of seven delay circuit elements, one delay circuit element associated with each lead carrying electrical signals produced by one of the transducer elements 12. One of the delay circuit elements, indicated by reference character 42 is illustrated in FIG. 5. It is to be understood that the delay circuit 42 of FIG. 5 is only one of seven such delays circuits, each connected to receive electrical signals from a particular transducer element 12, and that each delay element is identical to the delay element 42.

The remainder of the circuitry illustrated in block form in FIG. 5 as associated with the delay circuit element 42 is also repeated identically in connection with each of the unshown repetitions of the delay circuit 42. Thus, in the processing circuitry of the system S, the entire circuitry illustrated in FIG. 5 is repeated seven times, for each of the lines for transmitting electrical signals to the signal processing circuitry 24.

The delay circuit element 42 preferably comprises a charge coupled device (CCD). A CCD is an integrated circuit for transmitting an input signal to an output in steps along the way. The time between the occurrence of the input signal and the production of the output signal is a function of the frequency of a clocking signal applied to the CCD. As the frequency of the clocking signal applied to the CCD is increased, the time required for an input signal to traverse its way through the delay circuit element 42 to its output is decreased.

In FIG. 5, the delay circuit element 42 is illustrated as having an input from one of the lines extending from an output of a receiver 20, and an output which is directed to the summing amplifier circuitry 24. Clocking signals are applied to the delay circuit 42 by a voltage controlled oscillator 44. The voltage controlled oscillator 44 produces a frequency output whose frequency is an increasing function of the magnitude of an analog DC signal applied to the voltage controlled oscillator. The input of the voltage controlled oscillator is provided at the output of a digital-to-analog converter 46. The digital-to-analog converter 46 produces a DC analog output which is an increasing function of the value represented by a twelve bit digital word appearing at its input.

The digital input to the digital-to-analog converter 46 is provided by a random access memory 48. The random access memory 48 is a digital storage device capable of storing several hundred twelve bit binary words, each word being storable in a separately accessible address or storage "bin" of the random access memory (RAM). The binary word appearing at the output of the RAM is that binary word contained within that address storage bin of the RAM which is represented by the particular eight bit binary word which is input to the RAM.

Similarly, the respective delay time programs of the other delay circuit elements which are not specifically shown in FIG. 5 (but which are associated with the remaining electrical signal carrying leads from the other transducer elements 12) can also be controlled. Together, the various programs applied to the respective delay circuits can be so chosen to provide the electrical signals produced by the more centrally located annular transducer elements 12 with greater delay times than those associated with electrical signals produced by the more outwardly located transducer elements.

The signal processing circuitry 22 includes circuitry for generating a representation of a predetermined frequency for each of the predetermined program steps selected in succession by the program select circuitry 37. The processing circuitry 22 also includes circuitry for comparing the reference frequency representation with the actual frequency produced by the voltage controlled oscillator 44, during a sampling interval, and for adjusting or updating the frequencies represented in the respective address bins of the RAM 48 in accordance with that comparison.

More specifically, the circuitry for producing representations of reference frequencies for the various steps of the program includes a read only memory (ROM) 54. The ROM 54 is an integrated circuit chip which produces a unique binary output in response to a set of input signals which are impressed upon a plurality of ROM input terminals.

In this system, the inputs to the ROM are the eight bit words impressed in succession upon the RAM 48 by the program select circuitry 37. For each program step represented by a particular eight bit word, the ROM 54 produces a twelve bit binary word which represents exactly the frequency which is ideally desired for synthesization by the voltage controlled oscillator for that program step.

The circuitry for effecting the comparison between the ideal frequencies represented by the ROM 54 outputs and the actual output of the VCO 44 include a programmable counter 56, a constant frequency source 58, a stop-start circuit 60 and a counter-divider 62. The programmable counter 56 is a counter which is programmed to indicate when it has digitally counted a number of pulses equal to the number expressed by the twelve bit word produced by the ROM 54. The programmable counter 56 receives and counts eighty megahertz pulses from a fixed frequency source 58 during an operation period which is a function of the actual VCO frequency. If the number of pulses counted in the period of operation is less than the amount programmed into the programmable counter by the ROM (as the amount ideally expected if the VCO is operating at the proper frequency for the particular program step) the programmable counter, in conjunction with a NAND gate error detector 64 produces a signal directed to an up-down counter 66 which causes the address bin associated with the particular program step being counted to decrease the number held within that bin by one least significant bit. If the number of pulses from the source 58 counted by the programmable counter exceeds that programmed by the ROM, the twelve bit word directed from the counter to the ROM will be all logical "1" bits and they will actuate the NAND gate 64 to produce a signal to the up-down counter 66 which causes the addressed bin of the RAM 48 to increase the value of the number represented therein by one least significant bit.

The duration of the counting operation of the programmable counter 56 and ROM 54 is determined by the stop-start circuit 60 and the divider counter 62. Upon actuation, the divider counter 62 responds to signals from the VCO 44 to count down until a predetermined number of pulses (preferably 455) from the VCO 44 have been received, at which time the counter 62 actuates the stop-start circuit 60 to terminate the counting by the programmable counter of the 80 megahertz pulses from the fixed source 58. At this time, the programmable counter produces a twelve bit word which indicates whether the number of fixed frequency pulses which should ideally have occurred during the predetermined counting period, (expressed by the twelve bit word produced by the ROM in response to the identification of the program step) is on one hand less than, or on the other, equals or exceeds, the number of fixed frequency counts actually received.

The program select circuitry 37, the source 58, stop-start circuit 60 and divider counter 62 are actuated in response to the conjunctive operations of the timing control logic 34. In response to a signal from the system timer 38, the timing control logic actuates the eighty megahertz source 58 to begin delivering pulses to the programmable counter 56, and actuates the stop-start switch 60 to cause the programmable counter to begin to count down. The divider counter 62 is also actuated simultaneously with the actuation of the source 58 and stop-start circuit 60. The divider counter 62, upon receipt of a total of 455 pulses from the VCO 44, resets the stop-start switch 60 to turn off the programmable counter.

The timing control logic 34 is in turn actuated by a signal from the system timer 38. The system timer 38 thereby actuates the signal processing circuitry 22 to restart operation at a predetermined time relative to the initiation of each burst of incident acoustical energy from the transducer elements 12. More specifically, at a predetermined time after the burst has terminated the system timer actuates the signal processing circuitry and the remainder of the system S to "listen" for ultrasonic echoes, at a focal distance which recedes outwardly from the transducer at a rate which is substantially equal to the velocity of the acoustic wave front propagated by the transducer elements 12.

In practice, the frequency program established by the program select circuitry 37 constitutes a repetitive ascending stairstep function, consisting of a plurality of discrete frequency step levels, each step level having a use time, or step width, of the order of less than 100 microseconds.

Figure 6:
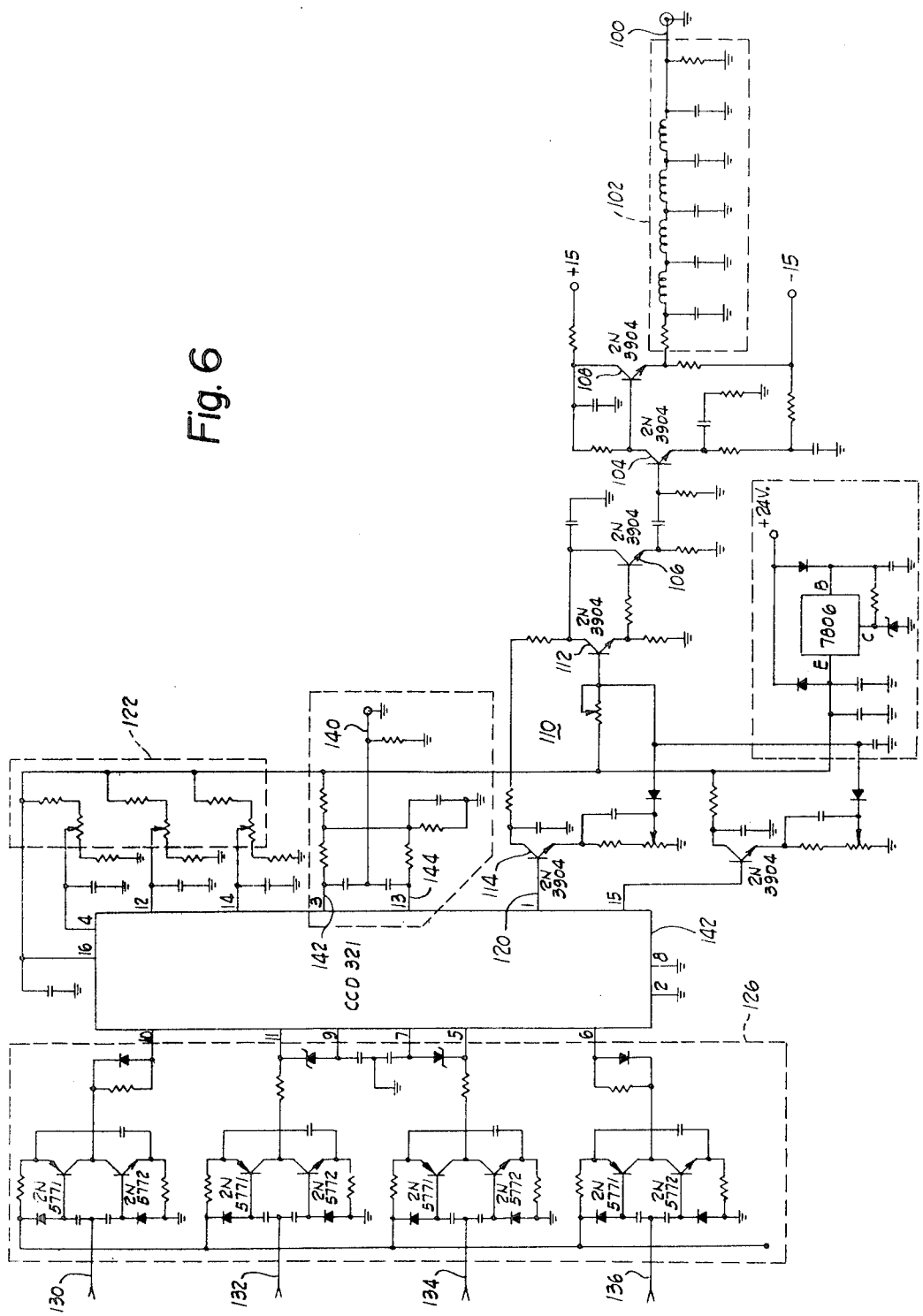
FIGS. 6-8 are schematic drawings illustrating in detail portions of the system represented in block form in FIG. 5.

The signal processing circuitry 22 and associated components, are shown in schematic form in FIGS. 6 through 8 and 10–11. FIG. 6 illustrates schematically the delay apparatus 42 and associated circuitry connecting it between the corresponding one of the receivers 20 and the Z axis summing amplifier 24.

The output signal from the delay element 42 appears at a terminal 100 after passing through a low pass filter 102, which serves to remove high frequency interference from the output signal. The low pass filter 102 is fed by a voltage amplifier 104 including transistors 106, 108 which in turn is fed by a current amplifier 110 consisting chiefly of transistors 112, 114. The output from the delay circuitry to the current amplifier 110 appears at a lead 120. The signal on the lead 120 represents the analog signal train from one of the receivers 20 which has been appropriately delayed by the delay circuitry element in response to clocking by the frequency program synthesized by the signal processing circuitry 22.

The delay element 42 is illustrated as preferably comprising a CCD321 charge coupled device manufactured by Fairchild Camera, Inc. of Mountain View, California.

Bias adjusting circuitry 122 is provided for adjusting the bias levels on the gates associated with the charge coupled device.

Voltage converter circuitry 126 is used to couple clocking signals to the delay device 42. The clocking signals appear on a set of input terminals 130, 132, 134, 136. The voltage converters serve to convert clocking signals from the 0 to 5 volt TTL design to 0 to 16 volt signals required for the charge coupled device 42. The input signals are directed to the charge coupled device 42 over a lead 140. The input signals appear on the input terminals 142, 144 of the charge couled device.

Figure 7:
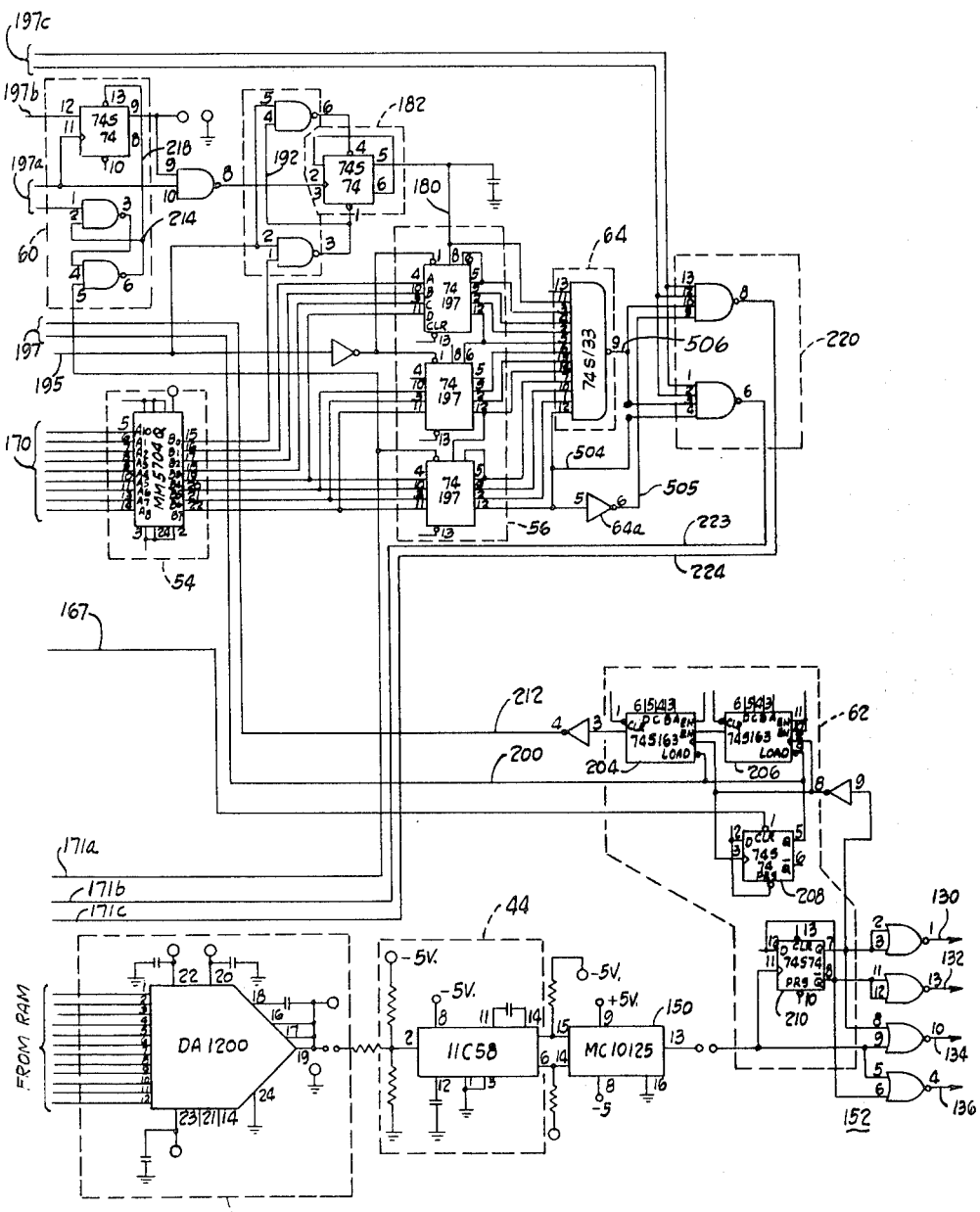
Figure 8:
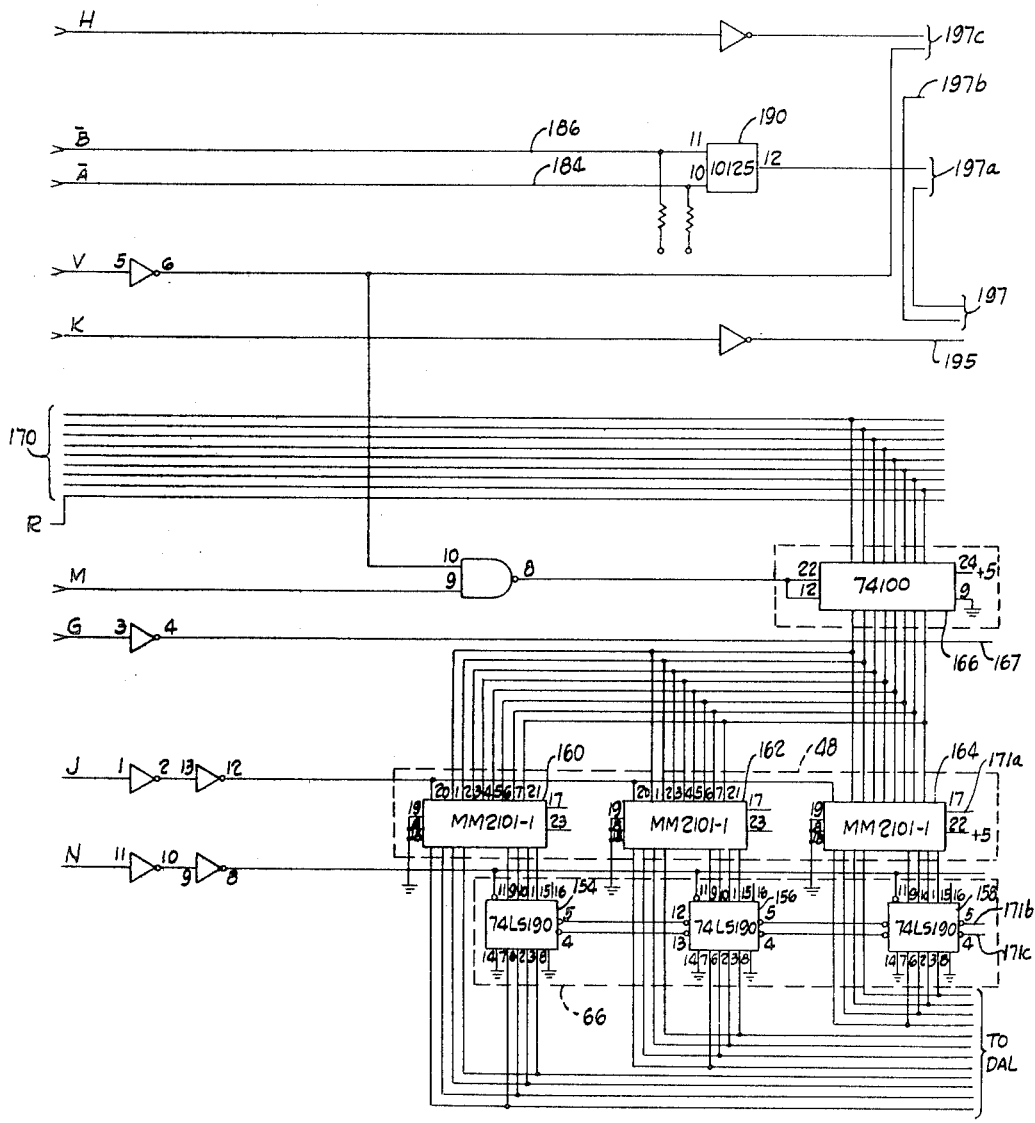

FIGS. 7 and 8 show schematically a portion of the signal processing circuitry 22. More specifically, in FIG. 7, the voltage control oscillator 44 is illustrated as principally comprising an integrated circuit designated by the chip No. 11C58. The output from the voltage control oscillator is directed through an ECL to TTL converter 150 and through gating and steering circuitry generally indicated at 152. The input to the voltage controlled oscillator 44 is from the output of a digital to analog converter 46 consisting primarily of a 12 input summing amplifier. When coupled to a RAM address bin, the 12 inputs of the summing amplifier consist of a twelve bit binary word which represents the value of the frequency stored in the addressed bin. The output signal from the RAM is held in latching circuitry including integrated circuit chips 154, 156, 158. (FIG. 8).

The ramdon access memory 48 comprises mainly three integrated circuit chips 160, 162, 164. Incoming signals to the random access memory consist of a series of eight bit binary words, each indicating a particular memory address of the RAM 48 corresponding to a predetermined program frequency step. When the input word to the RAM corresponds to a particular RAM address, the RAM is caused to produce at its outputs and hold in the latches the twelve bit binary word discussed earlier which represents the value of a signal frequency stored at that address and which corresponds to that program step represented by the eight bit binary word input to the RAM.

Each RAM input signal, representing a particular program step, is successively held in an eight bit latching circuit 166.

The program step indicated (RAM input) signals appear successively upon a set of leads 170. In addition to being directed to the RAM input latching circuitry 166, the program step indicated signals are also directed to the read only memory (ROM) 54. The ROM 54 generates an eight bit output which is a function of the program step address signal input thereto. The ROM 54 output is decoded to twelve bits in the programmable counter 56. (FIG. 7).

The ROM 54 and the programmable counter 56 operate in conjunction such that the programmable counter is programmed to count upwardly from a predetermined twelve bit number which is a representation of a frequency which is the desired frequency associated with the program step input number. Specifically, the twelve bit word to which the programmable counter is programmed is equal to the number of cycles from the fixed frequency source entering the programmable counter which would be ideally expected to so enter the programmable counter during the production of 455 cycles by the voltage controlled oscillator, provided that the voltage controlled oscillator is producing the frequency desired in conjunction with the program step indicated by the incoming program step signals. The programmable counter 56 is caused to count upwardly from the twelve bit number programmed into it in response to 40 megahertz clocking signals entering the programmable counter on a lead 180 from a divide by two circuit 182. The divide by two circuit is fed by the output from the fixed 80 megahertz source over a pair of leads 184, 186 (FIG. 8). The megahertz signal is passed through an ECL to TTL converter 190 where it passes through steering circuitry 192 on its way to the dividing circuit 182.

The count up by the programmable counter 56 is initiated by the circuitry 192 which in turn is actuated by a start signal appearing on a lead 200 whose production is initiated by the timing control circuitry.

During the count up by the programmable counter 56, dividing circuitry 62 counts the number of cycles produced at the output of the voltage controlled oscillator, and produces a stop signal output upon the production of 455 VCO cycles following the application fo the start signal. The dividing circuitry 62 is chiefly constituted by integrated circuit chips 204, 206, 208, 210. The counting circuitry 62 divides the output of the VCO by 455, and produces a stop signal on a lead 212 in response to the accumulation of 455 pulses from the VCO. The stop signal is keyed as an input to stop circuitry 214, which, in response thereto, produces a signal on a lead 218 which deactuates the start detector circuitry 192, causing the programmable counter to cease counting upwardly upon the expiration of the 455 VCO cycles.

The output from the programmable counter 56, a twelve bit binary word, is directed as the input to a twelve input NAND gate 64. When any of the inputs of the NAND gate 64 are a logical "0", the output of the NAND gate 64 is a logical "1". Thus, in any instance and as to any program step as to which the programmable counter 56 has counted upwardly and until the counter bit of the counter 56 has stopped at zero, the NAND gate produces a logical "1" output. This condition indicates that, for the particular program step involved, the number of signals from the fixed frequency source during the sampling period consisting of 455 VCO output pulses is incorrect.

If the number of counts is less than that programmed then the MSB of the programmable counter 56 (Line 504) will be a logical "1" indicating too high a frequency. If the number of counts is greater than that programmed then the MSB will be logical "0" indicating too low a frequency.

The information at the output of the NAND gate 64 (Line 506) is utilized to update the information in the RAM 48 representing the desired frequency which the VCO is caused to produce for the associated program step. If the logical signal is a "1", the value of the frequency represented in the particular RAM address bin for the associated program step is increased by one least significant bit. Conversely, if the logical signal is a zero, the value of the frequency represented in the particularly associated RAM address bin is decreased by one least significant bit. Thus, the output from the gate 64 (Line 506) is used to adjust appropriately the output frequency of the VCO 44. More specifically, the output signal from the gate 64 A (Line 505) is input to a set 220 of steering circuitry, which directs the signal over a pair of leads 222, 224 to the up/down counter 66.

The up/down counter 66 is associated with the RAM latching circuitry 48, as shown in detail in FIG. 8.

The operation and control of the processing circuitry 22 and delay elements 42 can best be understood by an analysis of a sequence of controlling input signals to the input terminals shown generally in the left-hand portion of the schematic drawing of FIG. 8. The terminals upon which these inputs appear are designated G, H, J, K, M, N, R, and V.

A logical "1" signal appears at the input V during periods in which the signal processing circuitry is to have its integrated circuit "chips" (FIGS. 7 and 8) enabled for operation. Consequently, for the relevant times discussed here, a logical "1" appears at the terminal V.

The signal processing circuitry can be operated in a so-called "operate" mode or a so-called "refresh" mode. In the operate mode, the program select circuitry sequentially addresses the RAM 48 to cause it to produce its sequence of program outputs to the digital-to-analog converter 46 and the voltage controlled oscillator 44, causing the voltage controlled oscillator to repeatedly produce the program of frequencies represented by the states of the various memory bins in the RAM. In the refresh mode, the programmable counter 56 and associated updating circuitry of the signal processing circuitry is operated to sample the various frequencies of the program produced by the voltage controlled oscillator and to update the contents of the RAM memory bins in accordance with the comparison between the program frequencies synthesized and the ideal frequency representations discussed above.

During the times in which an ultrasonic wave front from the transducer is penetrating a patient and producing ultrasonic echoes to be detected, the signal processing circuitry is operated in the "operate" mode. During so-called "dead time" intervals between production of an acoustic wave fronts and detection of its associated echoes, the signal processing circuitry is controlled to operate in the refresh mode. In this way, the contents of the RAM memory bins are updated vary frequently, during system dead time, to assure the maintenance of correct frequency representations in the RAM address bins.

Selection of operation mode occurs by way of the state of the logical input appearing at the terminal V. If the signal at the terminal V assumes a logical "0" value, the signal processing circuitry is caused to operate in the "refresh" mode. If the signal assumes a logical "1" value, the system operates in the "operate" mode.

The timing control logic 34 controls the signal on the terminal V to a logical "1" at periods within the intervals between the production and receipt of incident and reflected ultrasonic energy produced in response to operation of the transducer T.

Figure 9:
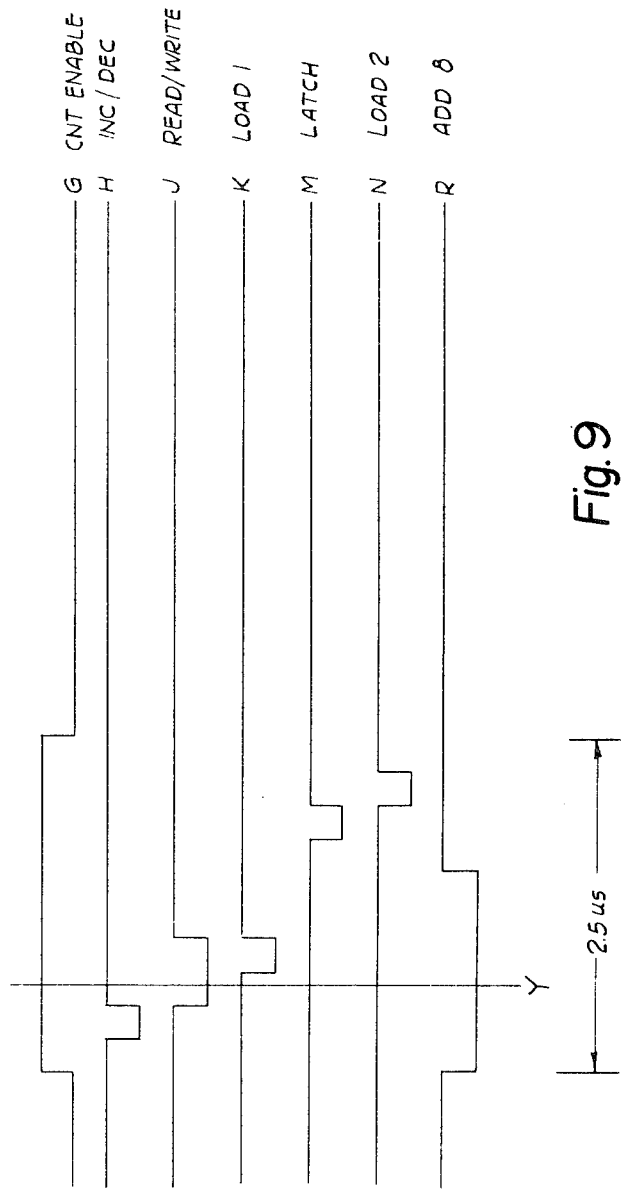
FIG. 9 is a timing diagram illustrating a sequence of operation of portions of the inventive system shown in FIGS. 6-8.

The time varying states of the signals to the terminals G, H, J, K, M, N, and R are best understood by reference to FIG. 9, which is a timing diagram graphically illustrating the relative states of these signals during system operation.

The state of the signal at the input G controls enabling the operation of the counters 56 and 62. When the signal at the terminal G assumes a logical "0" value, the counters are enabled for operation. When the signal at terminal G assumes a logical "1" value, the counters are disabled.

The state of the logical input signal appearing at the terminal R controls the loading of the program step into programmable counter 56. When R is a logical "0" the 8 LSB's are loaded into the programmable counter 56. This is effected by logic signal K as it transitions from a logical "1" to a "0" to a "1" (i.e. a pulse). When R becomes a logical "1" the 4 MSB's are enabled to be loaded into the programmable counter 56 by N as it transitions from a logical "1" to a "0" to a "1" (i.e. a pulse) causes 166 (74100) to latch address lines 0 thru 7 (represented by 8 lines #170 in FIG. 8). These latched address lines 170 cause the RAM 48 to access (from its stored memory) a 12 bit word. The 12 bit word is loaded into the up/down counters 66 by a logical "1" to "0" to "1" transition of line N. After a count cycle (a "0" transition of G) G returns to a logical "1" and the updating process begins. This is accomplished by a "1" to "0" to "1" transition of line H. The NAND gate 64 determines whether updating is necessary. If updating is necessary, lines 504 and 505 determine whether the updating is a up or down count. After up and down counting (66) is achieved a new 12 bit word (different by only 1 LSB) is loaded back into the memory location of the RAM 48 by a "1" to "0" to "1" transition of line J. This completes the "refresh" mode of operation.

In the "operate" mode the ROM 54, the programmable counters 56 and 62, NAND gate 64, steering circuitry 220 are disabled. Latch 166 is made into a through-put gate. Address lines 170 (0 thru 7) are stepped through a predetermined pattern by the program select 37. These address lines act as memory locations in the RAMS 48 which output 12 bit words previously obtained during the "refresh" mode. These 12 bit words are outputted to the up/down counters 66 which are used as latches during the "operate" mode. Line N with a "1" to "0" to "1" transition accomplishes this latching. The 12 bit words are outputted from the latches "66" to the digital to analog converter 46 which in turn generates the correct voltage for the voltage control oscillator 44 to synthesize the frequency which corresponds to the correct delay.

It is believed to be well within the capability of one of ordinary skill to provide timing control circuitry for effecting the signal patterns described by the timing diagram of FIG. 9 and in the disclosure above. However, for those not familiar with the particular art involved here, there is provided in FIGS. 10 and 11 a schematic diagram of appropriate circuitry embodying the timing control logic 34.

Figure 10:
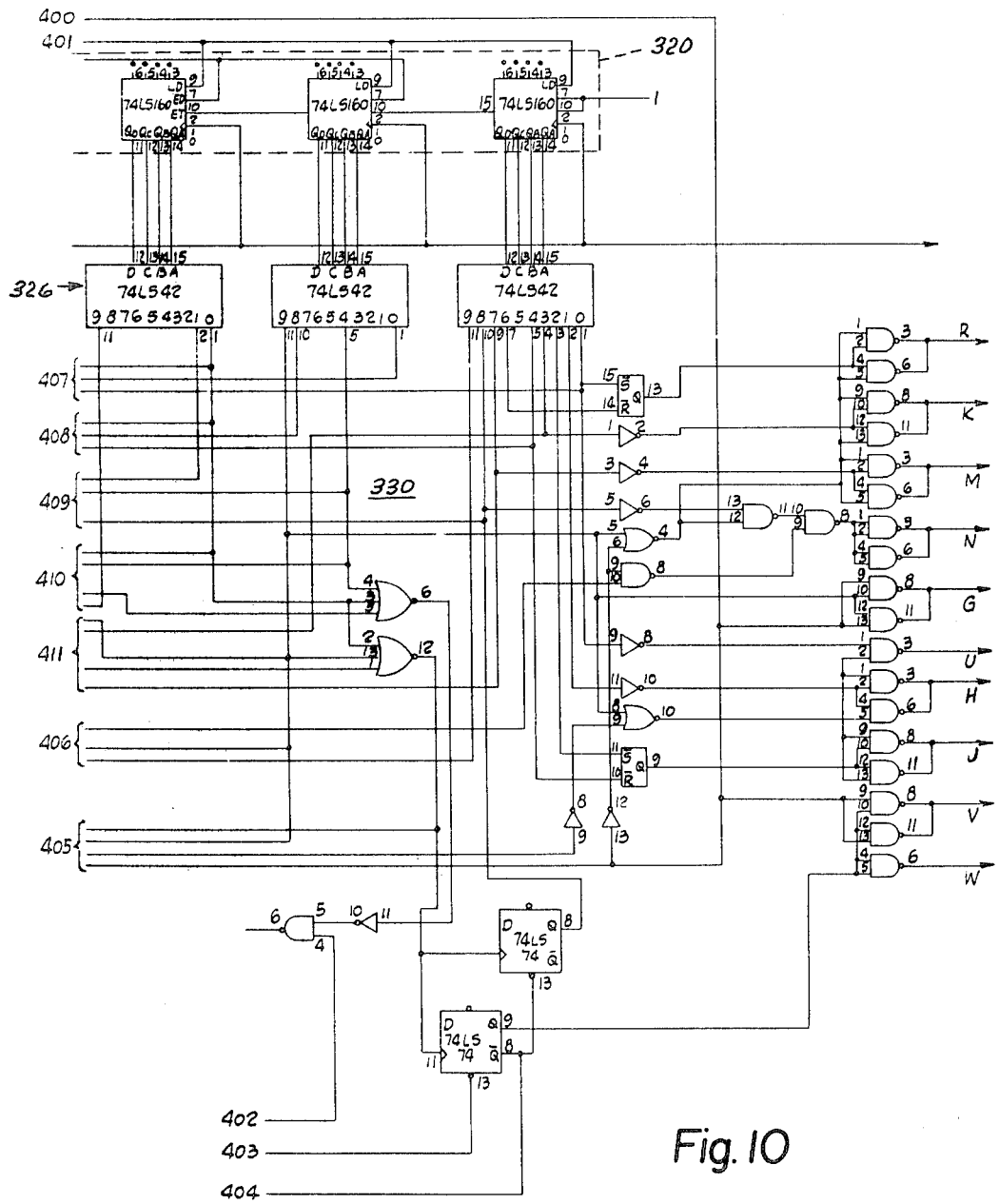
FIGS. 10-11 are schematic drawings illustrating further portions of the system represented in block form in FIG. 5.
Figure 11:
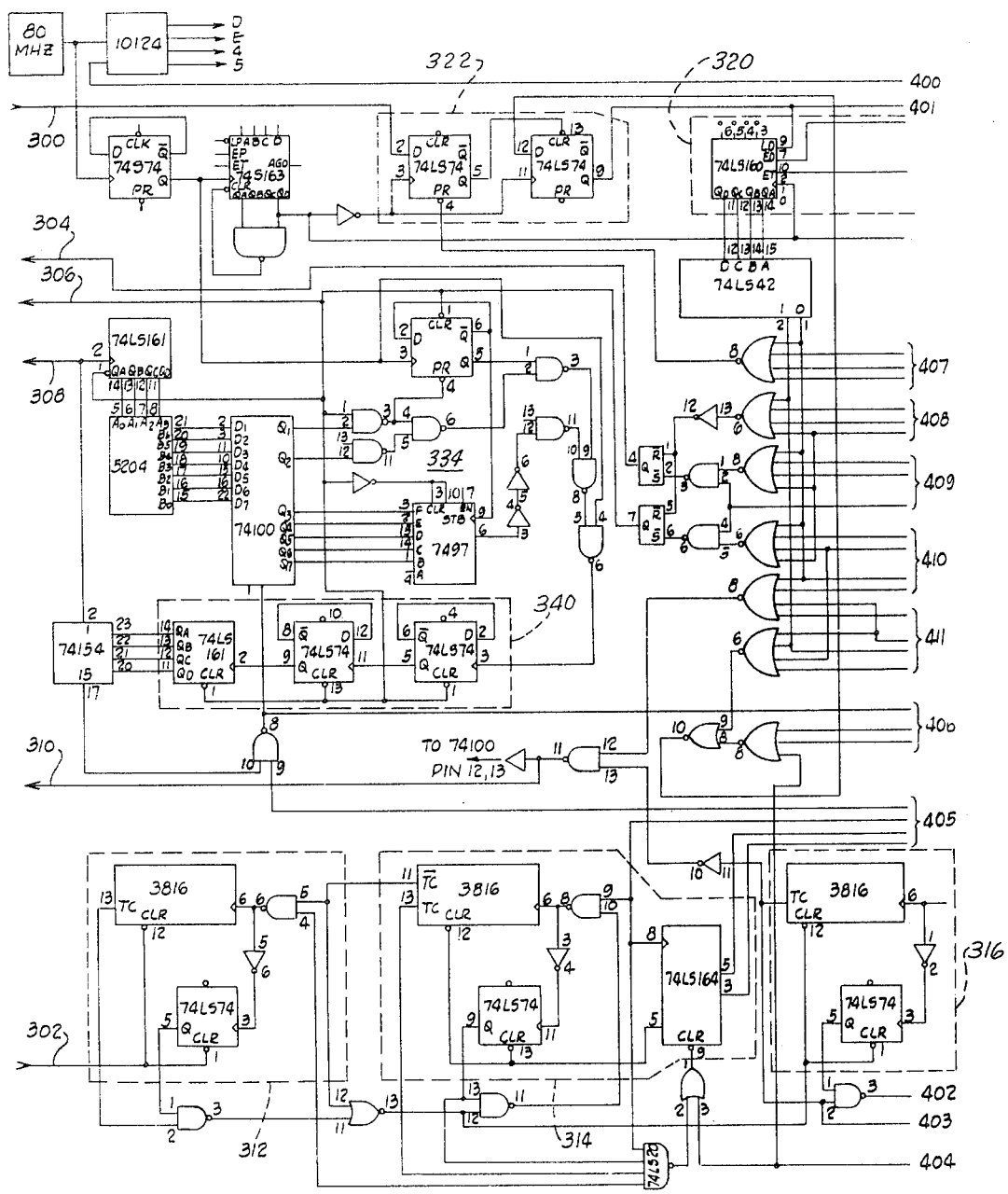

The timing control logic is illustrated in schematic form in FIGS. 10 and 11. Matching electrical leads linking the circuitry described in FIGS. 10 and 11 are designated with the reference characters 400-411.

In addition to the outputs to the signal processing circuitry 22 which has been described in detail above, the timing control logic has a selection of inputs and outputs, appearing generally in the left-hand portion of FIG. 11, which will now be described in detail. An input appearing on an electrical lead 300 indicates the presence or absence of a "run" signal from the program control circuitry 37. When the program control circuitry is actuated to step through a program by providing a predetermined sequences of RAM addresses, the timing control logic is actuated to an operable state by the "run" signal produced by the program control circuitry on the lead 300.

The system of this invention has a "warm-up" feature which is actuated by the presence of a trigger signal appearing on an input 302, illustrated in the lower left portion of FIG. 11. When a predetermined input signal occurs on the lead 302, warm-up circuitry in the timing control logic is actuated to cause the signal processing circuitry 22 to operate in the above-described "refresh" mode. This refresh mode is clocked by circuitry described below to repeatedly operate the signal processing circuitry in its refresh mode for a predetermined number of cycles.

The purpose of the warm-up is, by repeatedly operating the signal processing circuitry to update the RAM for a predetermined time, the RAM address bins are allowed to accumulate frequency representing data, up to a substantially steady state level. If this were not done, before the total system operation began, the RAM address bins would not, at least at the early portions of system operation, contain data which would accurately represent the frequencies desired for the program. The warm-up feature is designed to allow the build-up to steady state in the RAM before the full system operation is initiated.

Several outputs from the timing control logic are also illustrated in the left-hand portion of FIG. 11. A signal appearing on a lead 304 controls the unblanking of the electron beam used in the display cathode ray oscilloscope of the system. Another signal appearing at a lead 306 triggers the initiation of the horizontal and vertical sweep of the cathode ray oscilloscope to keep it in synchronization with operation of the rest of the system. The signal appearing at the lead 308 controls operation of a miroprocessor which is a portion of the program select circuitry 37. A signal appearing at a lead 310 is directed to the system timer 38 to properly synchronize its operation with that of the timing control logic in associated signal processing circuitry 22. The system timer 38, and the operation of the signals on the leads 304, 306, 308, 310 are analogous to the known operation exemplified by the above referenced system 80L of Picker Corporation.

Although the timing control logic is disclosed in schematic form in FIGS. 10 and 11, an explanation of various groups of components will assist those not intimately familiar with this art. The components generally enclosed in the dotted box designated 312 represent warm-up trigger circuitry. In response to a signal appearing at the input lead 302, the warm-up trigger circuitry 312 actuates other circuitry for effecting the warm-up period. Warm-up timer circuitry is generally enclosed in the dotted box labeled 314. The warm-up timer circuitry counts the number of cycles, or program repetitions, executed by the signal processing circuitry 22 during the warm-up period. When a predetermined number of such repetitions have occurred, the warm-up timer effects the termination of the warm-up period and the change-over to a normal operation, in which the system is operated in the so-called "operate" mode, with intervening "refresh" single cycles to update and correct the frequency representing data stored in the RAM.

Preferably, the warm-up period is determined to have a duration of approximately sixty seconds, to assure the achievement of approximate steady state in the address bins of the RAM. Since a complete refresh cycle (of 256 program steps) requires approximately 6450 microseconds, the warm-up period is predetermined by the duration of 4096 refresh cycles.

The circuitry indicated within the dotted blocks designated 316 constitutes a display counter. The display counter counts the number of display cycles, i.e., cycles occurring during the operate mode, which are executed between each refresh cycle. Preferably, the display counter 316 is preset such that one refresh cycle occurs after each train of one or more cycles of operation in the "operate" mode.

A system clock 320 is shown as a 16 bit system clock. The input to the clock which triggers its operation is the "run" signal appearing on the lead 300. Interposed between the lead 300 and the clock 320 is synchronization circuitry 322 which assures that the clock 320 begins operation in sync with the occurrence of the "run" signal.

The clock 320 feeds into converter circuitry 326. The converter circuitry 326 actuates the counting and steering circuitry generally designated at 330, to provide the outputs to the signal processing circuitry 22 whose timing characteristics are described in graphical form in FIG. 9.

The converter circuitry 326 also operates display decoding and steering circuitry generally indicated at 334. Smoothing circuitry 340 is provided for appropriately processing signals produced by the decoding circuitry 334.

The program select circuitry is easily provided by one of ordinary skill, comprising mainly a clocked ROM, which generates the predetermined sequence of delay frequency representations in accordance with the predetermined program.

It is to be understood that the embodiment of this invention is intended as illustrative rather than as exhaustive. One of ordinary skill could make certain modifications, alterations and changes to the embodiment shown without departing from the spirit of this invention or the scope of the appended claims.

What is claimed is:

1. A system for producing precisely frequency controlled clocking signals, said system comprising:
   (a) a frequency adjustable source for producing a succession of the clocking signals to be frequency controlled;
   (b) a reference generator having means for producing a reference signal representing a predetermined reference frequency;
   (c) comparator circuitry connected to the reference generator and to the source for sampling the electrical signals and having means for comparing their frequency with the reference frequency and for producing an error signal indicating a characteristic of the difference between the reference and sampled signal frequencies, and
   (d) correction circuitry including a random access memory and having means for subsequently adjusting the frequency of the clock signals in response to the error signal.

2. The system of claim 1, wherein:
said source comprises a voltage controlled oscillator.

3. The system of claim 1, wherein:
   (a) said comparator comprises a fixed frequency source and a programmable counter for counting cycles of the fixed frequency source occurring during a sampling interval;
   (b) said reference generator comprises:
   circuitry for programming said programmable counter for response to the receipt of a predetermined number of cycles of said fixed frequency during the sampling interval signals corresponding to a predetermined clocking frequency, and
   (c) said comparator further comprises:
   means for initiating operation of said programmable counter, said means including circuitry connecting the source with the programmable counter for delivering the fixed frequency signals to the programmable counter during the sampling interval.

4. The system of claim 3, wherein:
said counter produces as its output said error signal digitally indicating the sign of the difference between said predetermined number of fixed frequency signal cycles, and the number of said fixed frequency signals actually occurring during said sampling interval.

5. The system of claim 1, wherein:
   (a) said adjustable source comprises a voltage controlled oscillator, and
   (b) said correction circuitry comprises digital-to-analog converter between said random access memory and said voltage controlled oscillator for converting a digital signal representing corrected frequency information to analog form for application to said voltage controlled oscillator.

6. A system for producing a program of precisely frequency controlled electrical clocking signals including alternating signals frequency controlled according to a periodic step function having discrete levels and step widths, said system comprising:
   (a) a voltage controlled oscillator adjustable in frequency for producing said electrical clock signals to be frequency controlled;
   (b) a programmable digital counter for comparing representations of the frequency of signals sampled from said voltage controlled oscillator with a frequency represented by a reference signal;
   (c) a reference generator including programming circuitry coupled to the programmable counter for programming the counter to respond to the cumulative receipt of a predetermined frequency of clock signal cycles;
   (d) actuating circuitry for causing the counter to operate during a predetermined time increment defined within a step width of said step function, and being substantially less than 100 microseconds;
   (e) circuitry for presenting a representation of frequency of clock signals produced by said voltage controlled oscillator to said digital programmable counter for sampling the frequency of said clock signals during said predetermined time increment;
   (f) circuitry associated with said programmable counter for producing an error signal indicating the sign of the difference between the frequency of clock signals sampled during said time increment and said predetermined frequency of cycles;
   (g) a digital random access memory; and
   (h) a digital-to-analog converter connected between said random access memory and said voltage controlled oscillator for utilizing an error for correcting the frequency of the clocking signals in accordance with the difference represented by the error signal.

7. The system of claim 6, further comprising:
(a) control means for causing the iterative operation of the components of claim 6 for sampling the frequency of clock signals during each of a succession of time increments defined within step widths of said step function, and
(b) circuitry associated with said random access memory for updating the cumulative information in response to a succession of error signals generated during said iterative operations for providing stored signals precisely representing respective frequency levels associated with each of several step widths of the periodic step function during which said iterative sampling occurs.

8. A system for synthesizing a program of output signal frequencies, each frequency corresponding to a program step, said system comprising:
(a) an adjustable frequency generator;
(b) a multichannel random access memory having a set of address channels, each channel being allocated for digitally storing a representation of the frequency corresponding to one of said program steps;
(c) circuitry for applying signals stored in the address channels in a sequence for operating the adjustable frequency generator for producing the frequency program, and
(d) updating circuitry for adjusting values of stored frequency representations in the address channels to compensate for undesirable differences in the frequencies of the generated program from the predetermined program frequencies, said updating circuitry comprising:
(i) a fixed frequency source;
(ii) a clock for defining a predetermined time period which is a function of the frequency produced by the adjustable frequency generator at a selected program frequency step;
(iii) means for counting the number of cycles produced by the fixed frequency source during the predetermined period;
(iv) circuitry for producing a signal indicating a reference number of said fixed frequency cycles which would be ideally produced according to the predetermined program during the predetermined period at said selected program frequency step, and
(v) a comparator for adjusting the stored frequency representation relating to said selected program frequency step in response to the difference between said counted and reference numbers of cycles.

9. A method for synthesizing precisely frequency controlled electrical signals, wherein said electrical signals are frequency controlled substantially according to a periodic stairstep time function, each step having a discrete frequency level and step width time duration, said method comprising the steps of:
(a) producing a sucession of the electrical signals to be frequency controlled;
(b) sampling the frequency of the electrical signals by deriving a signal indicating the frequency of the electrical signals occurring during a time increment within one step width;
(c) comparing the sampled signal frequency with a reference signal representing a frequency;
(d) producing an error signal indicating a characteristic of the difference between the reference and sampled signal frequencies, and
(e) applying the error signal for adjusting the frequency of the electrical signals corresponding to said one step width, the initiation of said adjusting step being delayed until another step width time duration of said step function following said one step width duration.

10. A method for synthesizing precisely frequency controlled electrical clocking signals including alternating electrical signals frequency controlled according to a periodic step function having discrete frequency levels and step width durations, said method including the steps of:
(a) producing a succession of alternating frequency adjustable clock signals to be frequency controlled;
(b) sampling the frequency of the clock signals during a time increment substantially less than 100 microseconds, and within one of said step width durations;
(c) producing a representation of a reference frequency;
(d) comparing said sampled signal frequency with the frequency indicated by said reference frequency representation by the use of a digital counter;
(e) producing a digital error signal in response to the comparison step, the error signal indicating the sign of the difference between the reference and sampled signal frequencies, and
(f) applying the error signal for correcting the frequency of the clocking signals during a stepwidth duration of said step function having an associated frequency level which corresponds to that of the step width duration during which said sampling step was executed, and which is a part of the next subsequent period of the step function.

* * * * *

UNITED STATES PATENT AND TRADEMARK OFFICE
CERTIFICATE OF CORRECTION

PATENT NO. : 4,251,779

DATED : February 17, 1981

INVENTOR(S) : SEELEY C. KELLOGG, PHILIP J. PELUSO, and RICHARD B. BERNARDI

It is certified that error appears in the above—identified patent and that said Letters Patent is hereby corrected as shown below:

Column 1, line 52, "echos" should be --echoes--; line 60, "place" should be --plane--;
Column 9, line 29, "delays" should be --delay--;
Column 12, line 42, "ramdon" should be --random--;
Column 16, line 40, "miroprocessor" should be --microprocessor--

Signed and Sealed this

Fourteenth Day of July 1981

[SEAL]

*Attest:*

*Attesting Officer*

GERALD J. MOSSINGHOFF

*Commissioner of Patents and Trademarks*